(12) United States Patent
Williams

(10) Patent No.: US 9,387,201 B2
(45) Date of Patent: *Jul. 12, 2016

(54) METHODS OF PROVIDING ANTI-INFLAMMATION SUPPORT

(71) Applicant: RCP Development, Inc., Sarasota, FL (US)

(72) Inventor: Jonnie R. Williams, Bradenton, FL (US)

(73) Assignee: RCP Development, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/167,285

(22) Filed: Jan. 29, 2014

(65) Prior Publication Data

US 2014/0206656 A1    Jul. 24, 2014

Related U.S. Application Data

(62) Division of application No. 13/494,237, filed on Jun. 12, 2012, now abandoned.

(60) Provisional application No. 61/528,380, filed on Aug. 29, 2011.

(51) Int. Cl.
| | |
|---|---|
| *A61K 31/44* | (2006.01) |
| *A61K 31/07* | (2006.01) |
| *A61K 31/593* | (2006.01) |
| *A61K 31/444* | (2006.01) |
| *A61K 36/81* | (2006.01) |
| *A61K 31/4545* | (2006.01) |
| *A61K 47/22* | (2006.01) |
| *A23L 1/00* | (2006.01) |
| *A23L 1/03* | (2006.01) |
| *A23L 1/30* | (2006.01) |
| *A23L 1/303* | (2006.01) |

(52) U.S. Cl.
CPC .............. *A61K 31/444* (2013.01); *A23L 1/0017* (2013.01); *A23L 1/031* (2013.01); *A23L 1/30* (2013.01); *A23L 1/3002* (2013.01); *A23L 1/303* (2013.01); *A61K 31/07* (2013.01); *A61K 31/4545* (2013.01); *A61K 31/593* (2013.01); *A61K 36/81* (2013.01); *A61K 47/22* (2013.01); *A23V 2002/00* (2013.01)

(58) Field of Classification Search
USPC .................................................. 514/167, 334
See application file for complete search history.

(56) References Cited

U.S. PATENT DOCUMENTS

| | | | |
|---|---|---|---|
| 2,930,720 A | 3/1960 | Finberg | |
| 3,067,068 A | 12/1962 | Finberg | |
| 3,901,248 A | 8/1975 | Lichtneckert et al. | |
| 4,897,388 A * | 1/1990 | Malluche | A61K 31/59 |
| | | | 514/167 |
| 5,065,775 A | 11/1991 | Fagg | |
| 5,119,835 A | 6/1992 | Heemann et al. | |
| 5,276,043 A | 1/1994 | Lippiello et al. | |
| 5,387,416 A | 2/1995 | White et al. | |
| 5,512,306 A | 4/1996 | Carlsson et al. | |
| 5,525,351 A | 6/1996 | Dam | |
| 5,573,774 A | 11/1996 | Keenan | |
| 5,582,837 A | 12/1996 | Shell | |
| 5,760,049 A | 6/1998 | Viner | |
| 5,792,799 A | 8/1998 | Sherman-Gold | |
| 5,840,906 A | 11/1998 | Zoltewicz et al. | |
| 5,845,647 A | 12/1998 | O'Donnell, Jr. et al. | |
| 5,942,244 A | 8/1999 | Friedman et al. | |
| 5,945,107 A | 8/1999 | Hessel et al. | |
| 5,972,389 A | 10/1999 | Shell et al. | |
| 6,090,411 A | 7/2000 | Pillay et al. | |
| 6,166,032 A | 12/2000 | Viner | |
| 6,202,649 B1 | 3/2001 | Williams | |
| 6,210,710 B1 | 4/2001 | Skinner | |
| 6,217,903 B1 | 4/2001 | Skinner | |
| 6,311,695 B1 | 11/2001 | Williams | |
| 6,350,479 B1 | 2/2002 | Williams et al. | |
| 6,369,052 B1 | 4/2002 | Kellar et al. | |
| 6,497,234 B1 | 12/2002 | Coy-Herbert | |
| 6,534,527 B2 | 3/2003 | Wolfson et al. | |
| 6,541,043 B2 * | 4/2003 | Lang | A61K 31/07 |
| | | | 424/725 |
| 6,569,470 B2 | 5/2003 | Williams et al. | |
| 6,582,737 B2 | 6/2003 | Hirsh et al. | |
| 6,723,340 B2 | 4/2004 | Gusler et al. | |
| 6,929,811 B2 | 8/2005 | Williams et al. | |
| 7,115,285 B2 | 10/2006 | McKee et al. | |
| 7,279,184 B2 | 10/2007 | Gow et al. | |
| 7,294,353 B2 | 11/2007 | Gow et al. | |

(Continued)

FOREIGN PATENT DOCUMENTS

| | | | |
|---|---|---|---|
| EP | 0 567 251 | * | 7/1993 |
| EP | 0567251 A1 | | 10/1993 |
| JP | 2013-507104 | | 3/2013 |
| WO | 9962531 A1 | | 12/1999 |
| WO | 0187288 A2 | | 11/2001 |
| WO | 02076434 A2 | | 10/2002 |
| WO | 2010030887 A1 | | 3/2010 |
| WO | 2011042166 A1 | | 4/2011 |
| WO | 2011/119722 A2 | | 9/2011 |

OTHER PUBLICATIONS

Wollen et al. ("Alzheimer's Disease: The Pros and Cons of Pharmaceutical, Nutritional, Botanical, and Stimulatory Therapies, with a Discussion of Treatment Strategies from the Perspective of Patients and Practitioners". Alternative Medicine Review, 2010;15(3): 223-244).*

(Continued)

*Primary Examiner* — Shirley V Gembeh

(74) *Attorney, Agent, or Firm* — Banner & Witcoff, Ltd.

(57) ABSTRACT

This disclosure provides products, including pharmaceutical compositions and dietary supplements, which are useful for anti-inflammatory support.

4 Claims, 10 Drawing Sheets

(56) References Cited

U.S. PATENT DOCUMENTS

| | | | |
|---|---|---|---|
| 7,329,419 | B2 | 2/2008 | Yatcilla et al. |
| 8,207,346 | B2 * | 6/2012 | Puthiaparampil et al. .. 546/268.1 |
| 2002/0025300 | A1 | 2/2002 | Wolfson et al. |
| 2002/0054926 | A1 | 5/2002 | Williams et al. |
| 2004/0013752 | A1 | 1/2004 | Wolfson |
| 2004/0176469 | A1 | 9/2004 | Thomas |
| 2004/0198754 | A1 | 10/2004 | McKee et al. |
| 2005/0061339 | A1 | 3/2005 | Hansson et al. |
| 2005/0176777 | A1 | 8/2005 | Williams et al. |
| 2006/0004076 | A1 | 1/2006 | Patel et al. |
| 2007/0003636 | A1 | 1/2007 | Mach |
| 2010/0154810 | A1 | 6/2010 | Williams |
| 2012/0196899 | A1 | 8/2012 | Williams |
| 2012/0245202 | A1 | 9/2012 | Williams |

OTHER PUBLICATIONS

Glass et al. (Cell 140, 918-934, Mar. 19, 2010).*
Walker et al. (Current neurophamcology, (2007), 5, 232-243).*
Klegeris et al. (Current Opinion in Neurology (2007); 20351-2035).*
Boyles (WebMD Mar. 2011).*
Maden (Nature Reviews Neuroscience 8; 755-765; (2007).*
Minghetti Curr Opin Neurol 18:315-321 (2005).*
Drugs.com (2012) 3 pages.*
Ayers et al., "A general procedure for the enantioselective synthesis of the minor tobacco alkaloids nornicotine, anabasine, and anatabine," The AAPS Journal 2005, 2005, vol. 7, No. 3, pp. E752-E758.
Final Office Action mailed Nov. 21, 2013 for U.S. Appl. No. 13/235,860.
Final Office Action mailed Nov. 21, 2013 for U.S. Appl. No. 13/235,893.
International Preliminary Report on Patentability and Written Opinion for PCT/US2011/029613 mailed Sep. 25, 2012.
Roskamp Institute, Role of Anatabine (RCP006 from Rock Creek Pharmaceuticals) as an anti-inflammatory agent, 1 pg, dated Mar. 5, 2011.
Roskamp Institute, Anti-Inflammatory effects of RCP006, 1 pg., dated Jul. 27, 2011.
Roskamp Institute, News Release, Roskamp Institute to Begin Human Alzheimer' Clinical Trials With a Natural Compound in Tobacco, 1 pg., dated Oct. 7, 2010.
Hoeck et al., Medical Hypotheses, Will vitamin D supplementation ameliorate diseases characterized by chronic inflammation and fatigue?, vol. 76, pp. 208-213, dated 2011.
Kulie, et al. The Journal of the American Board of Family Medicine, Evidence-Based Clinical Medicine, Vitamin D: An Evidence-Based Review, vol. 22, No. 6, pp. 698-706, dated Nov. 1, 2009.
Aukrust, et al., European Journal of Clinical Investigation, Decreased vitamin A levels in common variable immunodeficiency: vitamin A supplementation in vivo enhances immunoglobulin production and downregulates inflammatory responses, vol. 30, No. 3, pp. 252-259, dated Mar. 1, 2000.
Austenaa, et al., Science Direct, Retinoic acid dampens LPS-induced NF-kappaB activity: results from human monoblasts and in vivo imaging of NF-kappaB reporter mice, vol. 20, No. 9, pp. 726-734, dated Sep. 1, 2009.

EP Appln. No. 12 82 8051, Supplementary European Search Report, dated Jan. 29, 2015.
McGilligan et al, The effect of nicotine in vitro on the integrity of tight junctions in Caco-2 cell monolayers, Food and Chemical Toxicology, vol. 45, 1593-1598, dated 2007.
Faessel, Report from the Roskamp meeting in Sarasota, Florida, www.benzinga.com/trading-ideas/long-ideas/11/06/1133694/dr-faessel-report-from-the-roskamp-meeting-in-sarasota-florid, dated Jun. 2, 2011.
CN Application No. 201280053394.6, Office Action, dated Jun. 2, 2015.
Brasier, "The NF-$\kappa$B Regulatory Network," Cardiovascular Toxicology, 2006, No. 6, pp. 111-130.
Denton, "Nicotine-related alkaloids and metabolites as inhibitors of human cytochrome P-450 2A6," Biochemical Pharmacology, 2004, No. 67, pp. 751-756.
Dobelis et al., "GABAergic Systems Modulate Nicotinic Receptor-Mediated Seizures in Mice," The Journal of Pharmacology and Experimental Therapeutics, 2003, vol. 306, No. 3, pp. 1159-1166.
Felpin, "Efficient Enantiomeric Synthesis of Pyrrolidine and Piperidine Alkaloids from Tobacco," J. Org. Chem., 2001, No. 66, pp. 6305-6312.
Felpin, "Total Synthesis of (S)-Anabasine and (S)-Anatabine," Synlett, 2000, No. 11, pp. 1646-1648.
Heck and de Mejia, "Yerba Mate Tea (Ilex paraguariensis): a Comprehensive Review of Chemistry, Health Implications, and Technological Considerations," J. Food Sci. Nov. 2007;72(9):R138-51.
International Search Report for PCT/US2011/040309 mailed Feb. 17, 2012.
International Search Report for PCT/US2012/035425, mailed Dec. 12, 2012.
International Search Report and Written Opinion for Serial No. PCT/US2012/042009 mailed Aug. 8, 2013, pp. 1-14.
Johansson et al., "Subclinical Hypervitaminosis A Causes Fragile Bones in Rats," Bone., 2002, vol. 31, No. 6, pp. 685-689.
Lanzetti, R.D. et al., Mate tea reduced acute lung inflammation in mice exposed to cigarette smoke, Nutrition, Feb. 2008, vol. 24, pp. 375-381.
Nizri et al., "Activation of the Cholinergic Anti-Inflammatory System by Nicotine Attenuates Neuroinflammation via Suppression of Th1 and Th17 Responses," The Journal of Immunology, 2009, vol. 183, No. 10, pp. 6681-6688.
Quan et al., "The Synthesis of Anatabine and Related Compounds," Synthesis of Anatabine, Aug. 1965, pp. 2769-2772.
Reifen, "Vitamin A as an anti-inflammatory agent," Proceedings of the Nutrition Society, 2002, vol. 61, pp. 397-400.
Shi, "Nicotinic Attenuation of Central Nervous System Inflammation and autoimmunity," The Journal of Immunology, 2009, pp. 1-10.
Wollen, "Alzheimer's Disease: The Pros and Cons of Pharmaceutical, Nutritional, Botanical, and Stimulatory Therapies, with a Discussion of Treatment Strategies from the Perspective of Patients and Practitioners," Alternative Medicine Review, vol. 15, No. 3, 2010, pp. 223-244.
JP Appn No. 2014-528385, Office Action, dated Dec. 14, 2015.

* cited by examiner

METHODS OF PROVIDING ANTI-INFLAMMATION SUPPORT

This application is a division of Ser. No. 13/494,237 filed on Jun. 12, 2012, which claims the benefit of and incorporates by reference Ser. No. 61/528,380 filed on Aug. 29, 2011.

DETAILED DESCRIPTION

Figure 1:
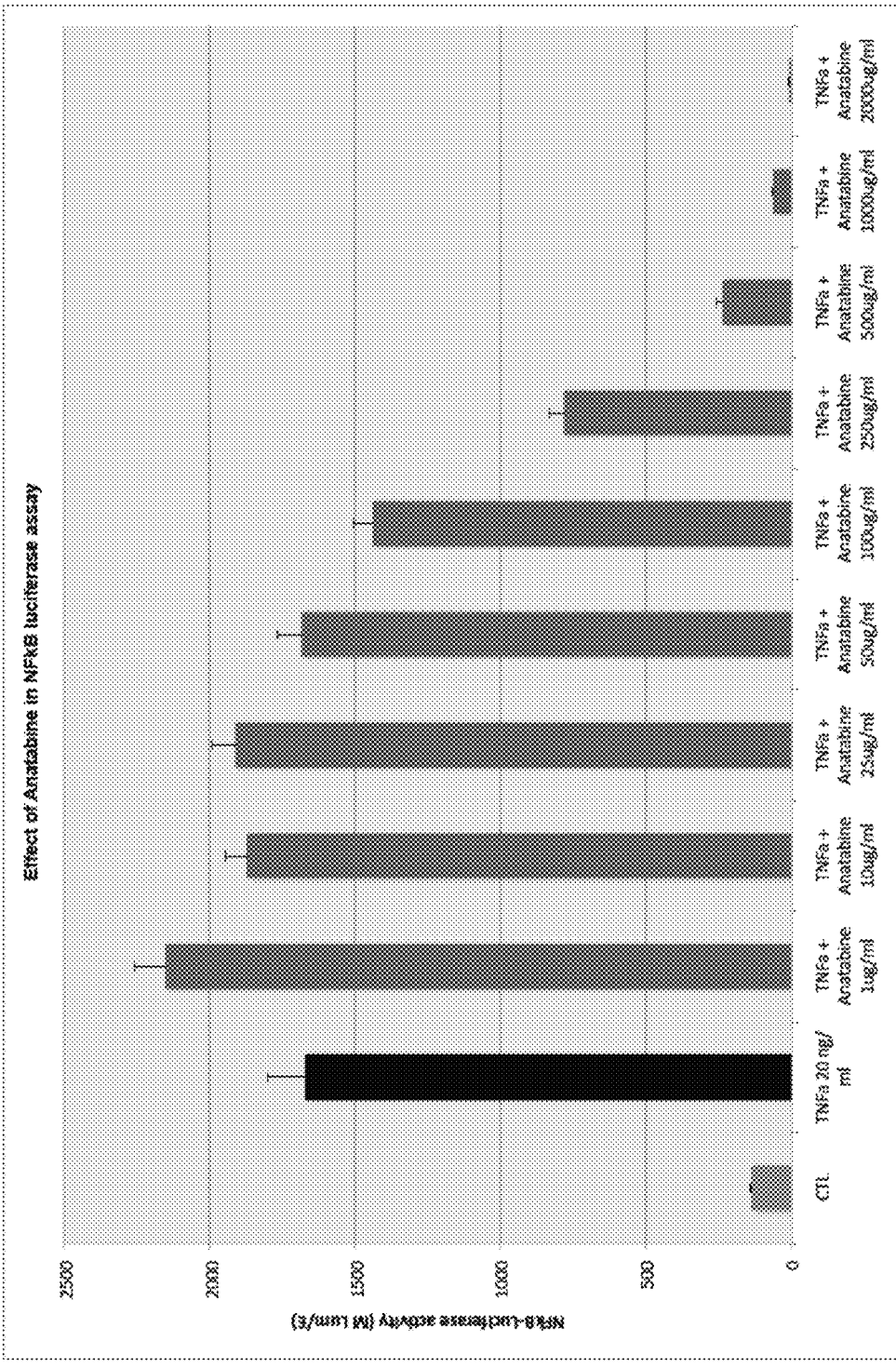
FIG. 1. Graph showing effects of anatabine on TNFα-induced NFκB activity in vitro.

Products comprising a compound of Formula I (e.g., anatabine), described below, and vitamins are useful for anti-inflammatory support. "Anti-inflammation support" as used herein includes helping the body to avoid excessive creation of inflammation, helping the body maintain lower levels of inflammation, helping the body maintain healthy levels of C-reactive protein, and the like. Products described herein can be, e.g., pharmaceutical compositions or dietary supplements. "Dietary supplement" as used herein includes the type of product identified in the United States as a "dietary supplement" in the Dietary Supplement Health and Education Act (DSHEA) of 1994, as well as the type of product identified in other parts of the world by terms such as "food supplements," "nutraceuticals," "functional foods," or simply "foods."

Products disclosed herein, including pharmaceutical compositions and dietary supplements, can be provided for administration to humans as well as to animals, such as a companion animal, a service animal, a farm animal, or a zoo animal. Such animals include, but are not limited to, canines (including dogs, wolves), felines (including domestic cats, tigers, lions), ferrets, rabbits, rodents (e.g., rats, mice), guinea pigs, hamsters, gerbils, horses, cows, pigs, sheep, goats, giraffes, and elephants.

In some embodiments, products (e.g., pharmaceutical compositions, dietary supplements) comprise a compound of Formula I, which can be provided as a pharmaceutically acceptable or food-grade salt:

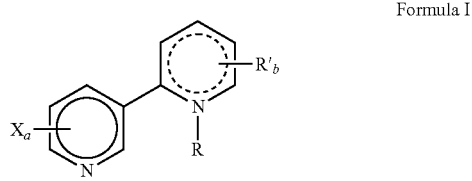

Formula I wherein:
R represents hydrogen or $C_1$-$C_5$ alkyl;
R' represents hydrogen or $C_1$-$C_7$ alkyl; and
X represents halogen or $C_1$-$C_7$ alkyl.
In some embodiments,
R represents hydrogen or $C_1$-$C_3$ alkyl;
R' represents hydrogen or $C_1$-$C_4$ alkyl; and
X represents halogen or $C_1$-$C_3$ alkyl.

The dotted line within the piperidine ring represents a carbon/carbon or carbon/nitrogen double bond within that ring, or two conjugated double bonds within that ring. One of the two conjugated double bonds can be a carbon/nitrogen double bond, or both of the conjugated double bonds can be carbon/carbon double bonds. When a carbon/nitrogen double bond is present, R is absent; and either (i) "a" is an integer ranging from 1-4, usually 1-2, and "b" is an integer ranging from 0-8, usually 0-4; or (ii) "a" is an integer ranging from 0-4, usually 0-2, and "b" is an integer ranging from 1-8, usually 1-4. When a carbon/nitrogen double bond is not present, R is present; "a" is an integer ranging from 0-4, usually 1-2; and "b" is an integer ranging from 0-8, usually 0-4 or 1-2. The term "alkyl," as used herein, encompasses both straight chain and branched alkyl. The term "halogen" encompasses fluorine (F), chlorine (Cl), bromine (Br), and iodine (I).

Table 1 below illustrates non-limiting examples of compounds within Formula I:

TABLE 1

| R | R' (position) | X (position) | a | b |
|---|---|---|---|---|
| H | $CH_3$ (3) | — | 0 | 1 |
| $CH_3$ | — | $CH_3$ (5) | 1 | 0 |
| H | — | $CH_3CH_2$ (4) | 1 | 0 |
| $CH_3CH_2$ | $CH_3$ (4) | — | 0 | 1 |
| H | $CH_3$ (2) $CH_3CH_2$ (5) | — | 0 | 2 |
| H | $CH_3$ (3) | $CH_3$ (5) | 1 | 1 |
| $CH_3$ | — | $CH_3$ (2) $CH_3$ (5) | 2 | 0 |

Compounds of Formula I may be present in the form of a racemic mixture or, in some cases, as an isolated enantiomer, such as illustrated below in Formula IA.

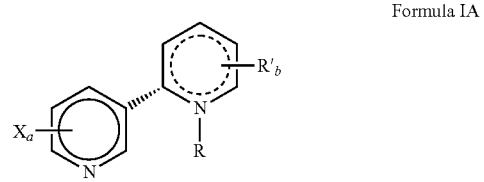

Formula IA

An example of a compound of Formula I is anatabine. The chemical structure of anatabine (1,2,3,6-tetrahydro-[2,3']bipyridinyl) is illustrated below, in which * designates an asymmetric carbon.

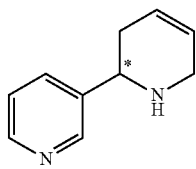 [SMILES: C1=CCC(c2cccnc2)NC1]

Anatabine exists in tobacco and certain foods, including green tomatoes, green potatoes, ripe red peppers, tomatillos, and sundried tomatoes, as a racemic mixture of R-(+)-anatabine and S-(−)-anatabine, whose structures are illustrated below.

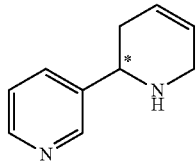 [SMILES: C1=CCC(c2cccnc2)NC1]

An example of a compound of Formula IA is S-(−)-anatabine. In some embodiments anatabine is provided in the form of a pharmaceutically acceptable (or food grade) salt of anatabine. Anatabine may be adsorbed on a cation exchange resin such as polymethacrilic acid (Amberlite IRP64 or Purolite C115HMR), as described in U.S. Pat. No. 3,901,248, the disclosure of which is hereby incorporated by reference in its entirety. Such cation exchange resins have been used commercially, for example, in nicotine replacement therapy, e.g., nicotine polacrilex.

Unless otherwise clear from context, the term "anatabine" as used herein refers collectively to anatabine, either as a racemic mixture or an enantiomer, and pharmaceutically acceptable or food-grade salts of either of them. In general, salts may provide improved chemical purity, stability, solubility, and/or bioavailability relative to anatabine in its native form. Non-limiting examples of possible anatabine salts are described in P. H. Stahl et al., *Handbook of Pharmaceutical Salts: Properties, Selection and Use*, Weinheim/Zürich: Wiley-VCHNHCA, 2002, including salts of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid.

As an alternative to preparing anatabine synthetically, anatabine can be obtained by extraction from tobacco or other plants, such as members of the Solanaceae family, such as datura, mandrake, belladonna, capsicum, potato, nicotiana, eggplant, and petunia. For example, a tobacco extract may be prepared from cured tobacco stems, lamina, or both. In the extraction process, cured tobacco material is extracted with a solvent, typically water, ethanol, steam, or carbon dioxide. The resulting solution contains the soluble components of the tobacco, including anatabine. Anatabine may be purified from the other components of the tobacco using suitable techniques such as liquid chromatography.

As part of the purification process, tobacco material may be substantially denicotinized to remove a majority of other alkaloids such as nicotine, nornicotine, and anabasine. Denicotinizing is usually carried out prior to extraction of anatabine. Methods that may be used for denicotinizing tobacco materials are described, for example, in U.S. Pat. No. 5,119,835, the disclosure of which is hereby incorporated by reference. In general, tobacco alkaloids may be extracted from tobacco material with carbon dioxide under supercritical conditions. The tobacco alkaloids may then be separated from the carbon dioxide by dissolving an organic acid or a salt thereof, such as potassium monocitrate, in the carbon dioxide.

In some aspects, an isolated form of anatabine is used. An "isolated form of anatabine," as used herein, refers to anatabine that either has been prepared synthetically or has been substantially separated from plant materials in which it occurs naturally. The isolated form of anatabine should have a very high purity (including enantiomeric purity in the case where an enantiomer is used). In the case of synthetic anatabine, for example, purity refers to the ratio of the weight of anatabine to the weight of the end reaction product. In the case of isolating anatabine from plant material, for example, purity refers to the ratio of the weight of anatabine to the total weight of the anatabine-containing extract. Usually, the level of purity is at least about 95%, more usually at least about 96%, about 97%, about 98%, or higher. For example, the level of purity may be about 98.5%, 99.0%, 99.1%, 99.2%, 99.3%, 99.4%, 99.5%, 99.6%, 99.7%, 99.8%, 99.9%, or higher.

In some embodiments, products (e.g., pharmaceutical compositions and dietary supplements) comprise synthetic anatabine. In some embodiments, products (e.g., pharmaceutical compositions and dietary supplements) comprise naturally occurring anatabine (i.e., anatabine extracted from a plant, as described in more detail below).

Vitamins and Minerals

Products (e.g., pharmaceutical compositions, dietary supplements) disclosed herein also contain one or more vitamins, such as Vitamin A (retinol), Vitamin B1 (thiamine), Vitamin C (ascorbic acid), Vitamin D (calciferol), Vitamin D2 (ergocalciferol), Vitamin D3 (cholecalciferol), Vitamin B2 (riboflavin), Vitamin E (tocopherol), Vitamin B12 (cobalamins), Vitamin K1 (phylloquinone), Vitamin B5 (pantothenic acid), Vitamin B7 (biotin), Vitamin B6 (pyridoxine), Vitamin B3 (niacin), Vitamin B9 (folic acid). Methods of synthesizing vitamins are well known, and vitamins can be obtained from any reputable commercial source. In some embodiments, products (e.g., pharmaceutical compositions, dietary supplements) contain synthetic or naturally occurring anatabine (or other compound of Formula I) and Vitamin A. In some embodiments, products (e.g., pharmaceutical compositions, dietary supplements) contain Vitamin D3. In some embodiments, products (e.g., pharmaceutical compositions, dietary supplements) contain Vitamin A and Vitamin D3.

Products disclosed herein (e.g., pharmaceutical compositions, dietary supplements) optionally can contain one or more other nutrients, such as pantothenic acid, calcium, iron, phosphorus, iodine, magnesium, zinc, selenium, copper, manganese, chromium, molybdenum, chloride, potassium, boron, nickel, silicon, vanadium, or lutein.

Additional Components

Additional components ingredients may be added to products (e.g., pharmaceutical compositions, dietary supplements) to improve taste or stability. Optionally, other components such as sweetening and flavoring agents may be added. Additional components include, but are not limited to, sweeteners, natural flavorants, artificial flavorants, colorants, antioxidants, preservatives, chelating agents, viscomodulators, tonicifiers, odorants, opacifiers, suspending agents, binders, thickeners, and mixtures thereof, including, but not limited to, xanthum gum, carboxymethylcellulose, carboxyethylcellulose, hydroxypropylcellulose, methylcellulose, microcrystalline cellulose, starches, dextrins, fermented whey, tofu, maltodextrins, polyols (including sugar alcohols, such as sorbitol or mannitol), carbohydrates (e.g., lactose), propylene hlycol alginate, gellan gum, guar, pectin, tragacanth gum, gum acacia, locust bean gum, gum arabic, gelatin, mannitol, natural and/or artificial mint flavors, sucralose, silicon dioxide, stearic acid, hydroxypropyl methylcellulose, magnesium stearate, titanium dioxide, natural glaze, methylparaben, propylparabens, triethyl citrate, citric acid, butylated hydroxytoluene (BHT), mono and diglycerides, polysorbate 80, and the like.

Forms

Products (e.g., pharmaceutical compositions, dietary supplements) disclosed herein may be in many forms to be taken orally, such as pills, tablets, capsules, soft gels, gelcaps, liquids, syrups, suspensions, powders, chews, lozenges, gum, bars, etc., or to be administered by other routes, such as parenterally, by inhalation spray, topically, via an implanted reservoir, etc. They can be prepared to be administered in foods or beverages. They can be supplied as a dried or powdered product for reconstitution with water or other suitable vehicle before use (e.g., milk, fruit juice, and the like).

Optionally, products disclosed herein (e.g., pharmaceutical compositions, dietary supplements) may be provided in a time-release formulation to provide anti-inflammatory support over extended periods. Extended release formulations are known in the art. For example, swellable particles are taught in U.S. Pat. Nos. 5,582,837, 5,972,389, and 6,723,340. Polymer matrices are taught in U.S. Pat. Nos. 6,210,710, 6,217,903, and 6,090,411. Typical materials used for extended release formulations are the polymers poly(ethylene oxide) and hydroxypropyl methylcellulose. Tablet formulations for slow release are also described in U.S. Pat. No. 5,942,244.

Packaging

Products disclosed herein (e.g., pharmaceutical compositions, dietary supplements) can be prepared, packaged, and labeled for use for anti-inflammation support.

Preparation of Products

Products disclosed herein (e.g., pharmaceutical compositions, dietary supplements) as disclosed herein may be prepared by any suitable technique and is not limited by any particular method for production. For example, anatabine (or another compound of Formula I) and vitamins can be combined with excipients and a binder, and then granulated. The granulation can be dry-blended with any remaining ingredients and compressed into a solid form such as a tablet.

The amount of anatabine (or another compound of Formula I) and vitamins in products (e.g., pharmaceutical compositions, dietary supplements) may vary. In some embodiments, the amount of anatabine (or another compound of Formula I) ranges from about 0.1 mg to about 10 mg (e.g., about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, or 10 mg). Anatabine (or another compound of Formula I) can be provided as free base or in the form of a salt, such as a citrate salt.

In some embodiments, the amount of Vitamin A ranges from about 200 to about 500 IU (e.g., about 200, 250, 300, 350, 400, 401, 402, 403, 404, 405, 406, 407, 408, 409, 410, 411, 412, 413, 414, 415, 416, 417, 418, 419, 420, 450, 475, or 500 IU). Vitamin A can be provided, for example, as retinyl acetate.

In some embodiments, the amount of Vitamin D3 ranges from about 15 IU to about 50 IU (e.g., about 15, 20, 25, 26, 27, 28, 29, 30, 31, 32, 33, 34, 35, 40, 45, or 50 IU). Vitamin D3 can be provided as cholecalciferol.

In some embodiments anatabine (or another compound of Formula I) and Vitamin A are provided in equal proportions (e.g., 1 mg each).

In some embodiments, one or two lozenges containing 1 mg anatabine (or another compound of Formula I) can be taken once, twice, or three times daily. In some embodiments, daily doses do not exceed 1, 2, 3, 4, 5, or 6 lozenges. In some embodiments, daily doses can exceed 1, 2, 3, 4, 5, or 6 lozenges.

In some embodiments a product is in the form of a lozenge that contains 1 mg anatabine (as anatabine citrate), 417 IU Vitamin A (as retinyl acetate), 33 IU Vitamin D3 (as cholecalciferol), and mannitol, natural and artificial mint flavors, sucralose, silicon dioxide, stearic acid, hydroxypropyl methylcellulose, magnesium stearate, titanium dioxide, natural glaze, methyl parabens, propylparabens, triethyl citrate, citric acid, BHT, mono and diglycerides, and polysorbate 80. In one embodiment this product is a dietary supplement ("ANATABLOC™").

Example 1

NFκB-Mediated Transcription Assays; Cytotoxicity Assays

The effect of a range of doses of anatabine, nicotine, crude extract of smokeless tobacco, and alkaloid extract of smokeless tobacco was examined in an NFκB luciferase assay (inhibition of TNFα-induced NFκB activity). The smokeless tobacco used in these experiments was plain long-leaf Copenhagen tobacco purchased from a local vendor. Crude extract was extracted with methanol and water and clarified by centrifugation and filtration. The alkaloid extract was prepared from sodium hydroxide and methanol extraction, organic phase separation and purification. All treatment samples were prepared as a function of weight (μg/ml), and all samples were diluted in DMSO. Dilutions were made immediately before cell culture treatments and, in all cases, the final amount of DMSO did not exceed 1% in cell culture media.

Figure 2:
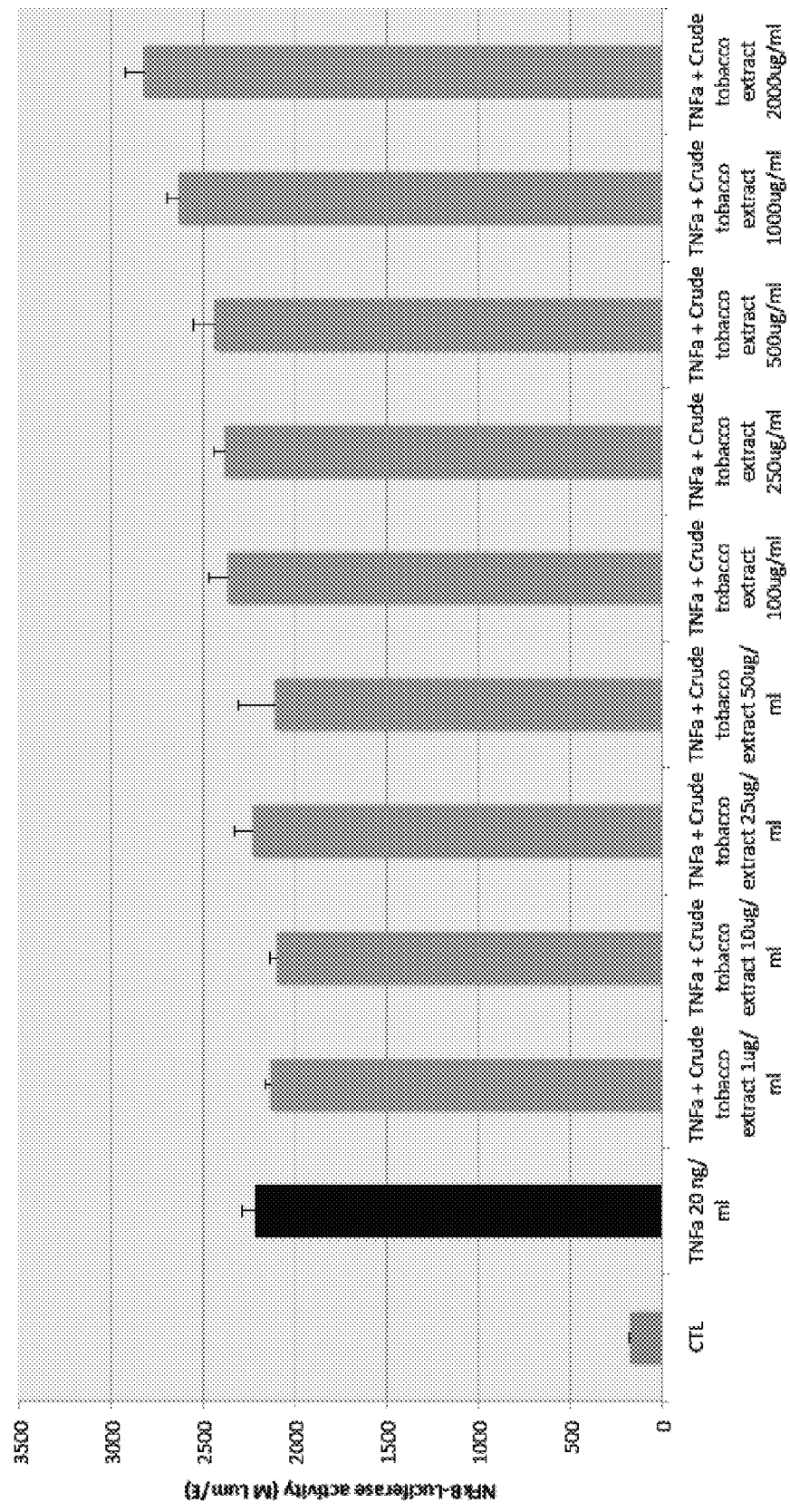
FIG. 2. Graph showing effects of a crude extract of smokeless tobacco on TNFα-induced NFκB activity in vitro.
Figure 3:
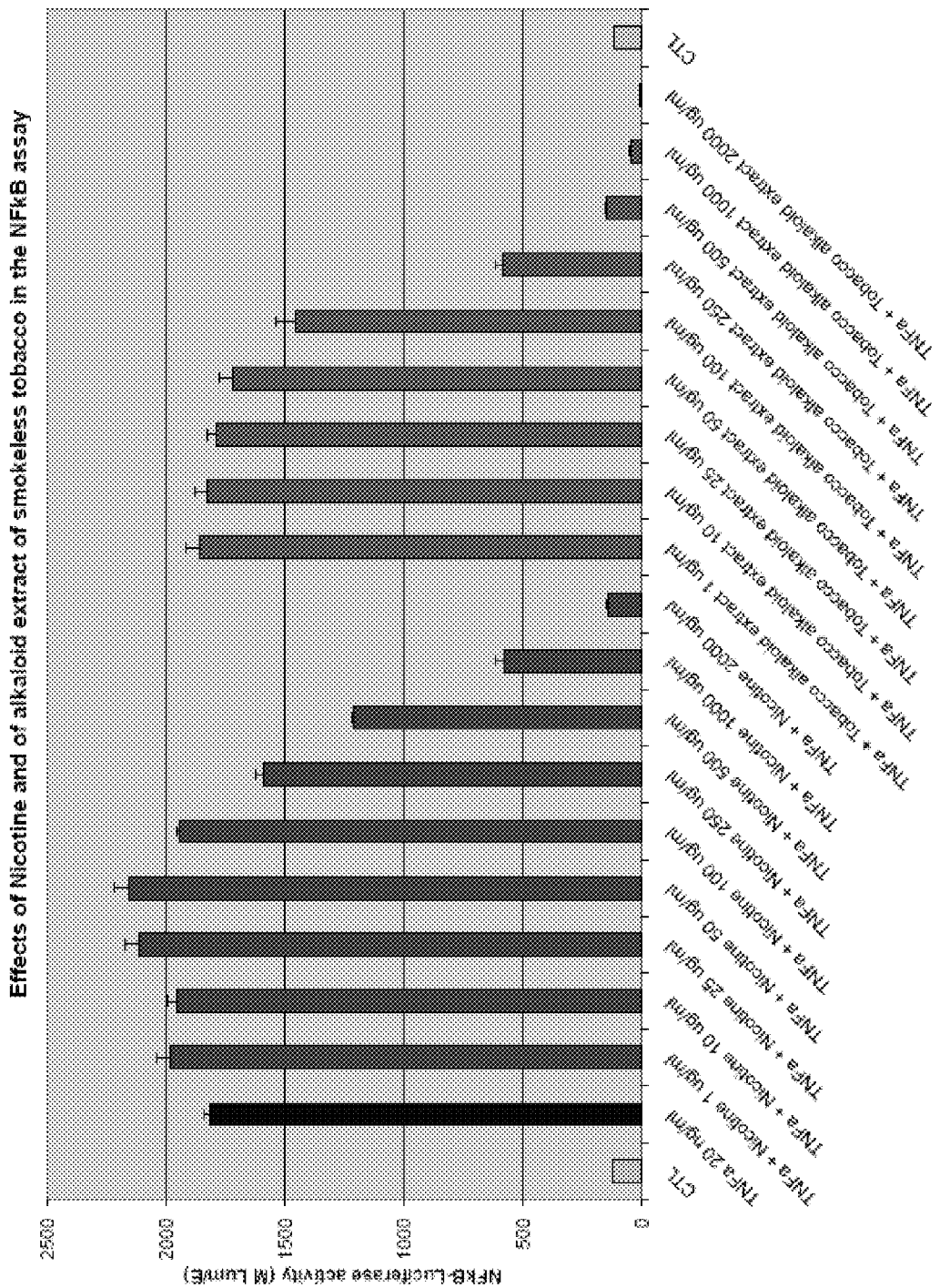
FIG. 3. Graph showing effects of nicotine and of an alkaloid extract of smokeless tobacco on TNFα-induced NFκB activity in vitro.

Human endothelial kidney cells (HEK293) transfected with an NFκB luciferase reporter were challenged with TNFα for three hours, then samples were applied to the challenged cells. The results are shown in FIGS. 1-3.

Cytotoxicity assays using the supernatants from the treated cells were conducted using an LDH Cytotoxicity Detection Kit (Roche) according to the manufacturer's instructions. The results are shown in FIGS. 4-6.

Figure 4:
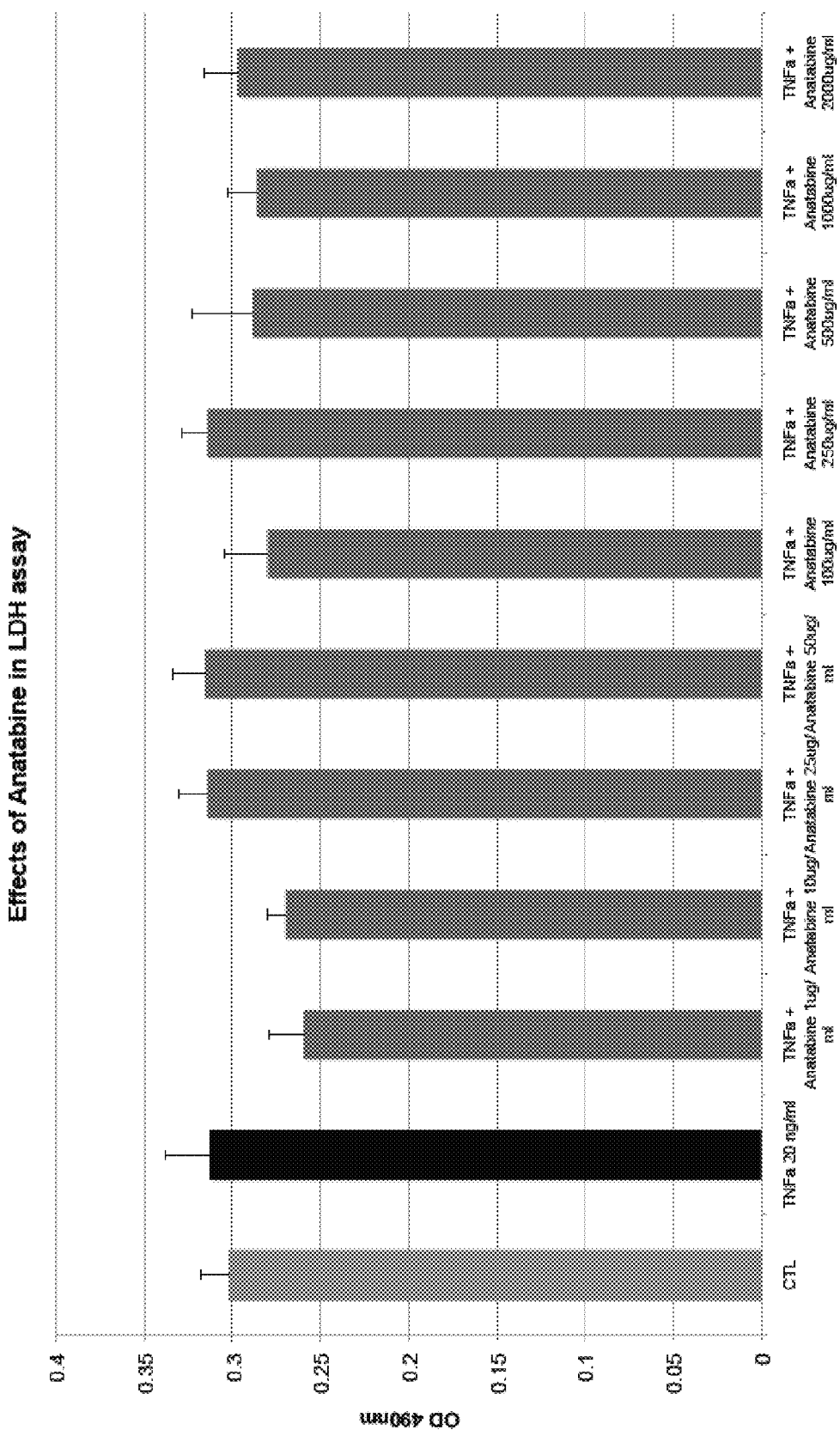
FIG. 4. Graph showing the results of a cytotoxicity assay measuring release of lactate dehydrogenase (LDH) using supernatant from the cells assayed in FIG. 1.
Figure 5:
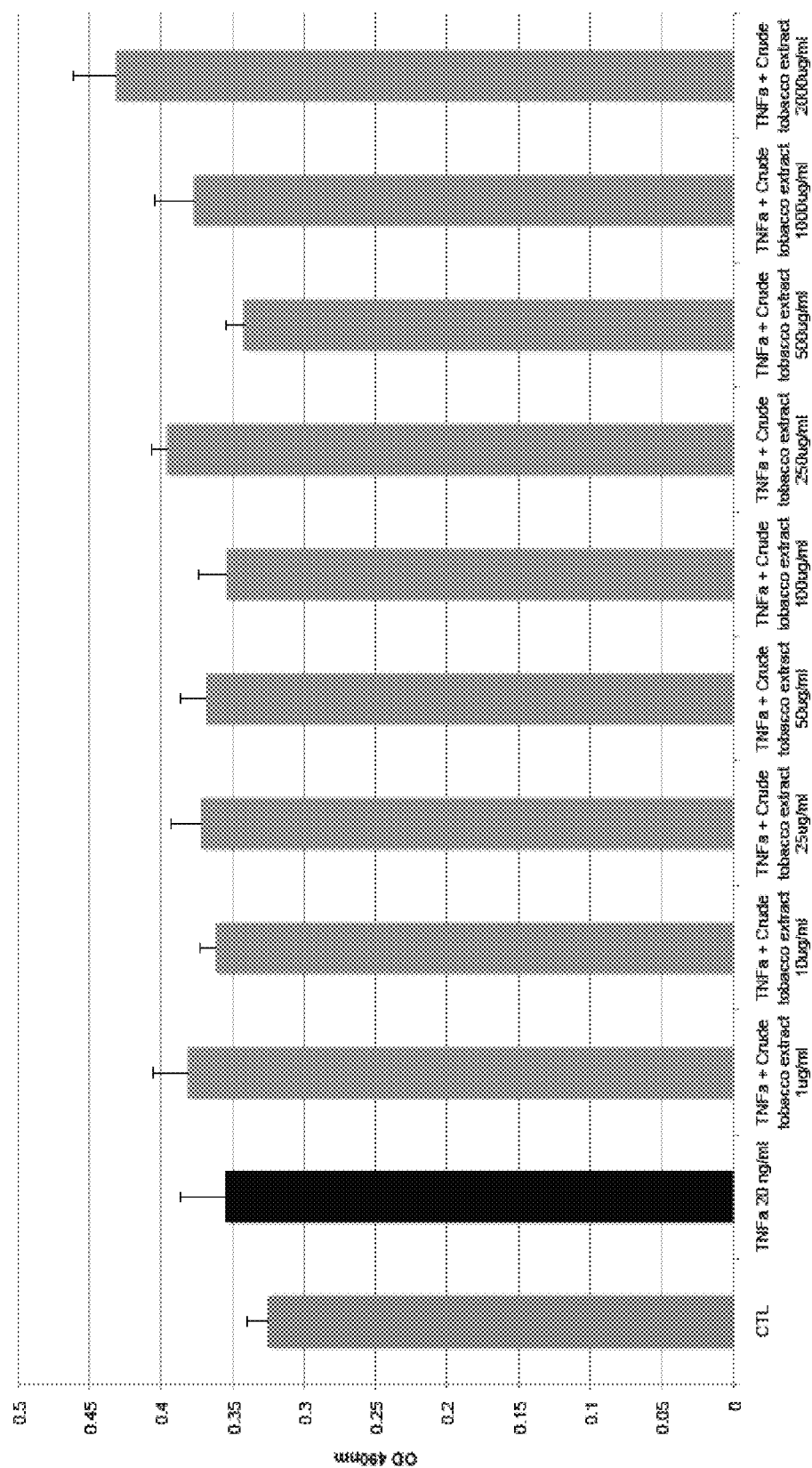
FIG. 5. Graph showing the results of a cytotoxicity assay using supernatant from the cells assayed in FIG. 2.

As shown in FIG. 1, TNFα induces an increase in NFκB-mediated transcription of luciferase; administration of anatabine can reduce this transcription to control levels without cellular toxicity (FIG. 4). Crude extracts of smokeless tobacco, while not toxic to cells (FIG. 5), do not reduce TNFα-induced NFκB-mediated transcription (FIG. 2).

Figure 6:
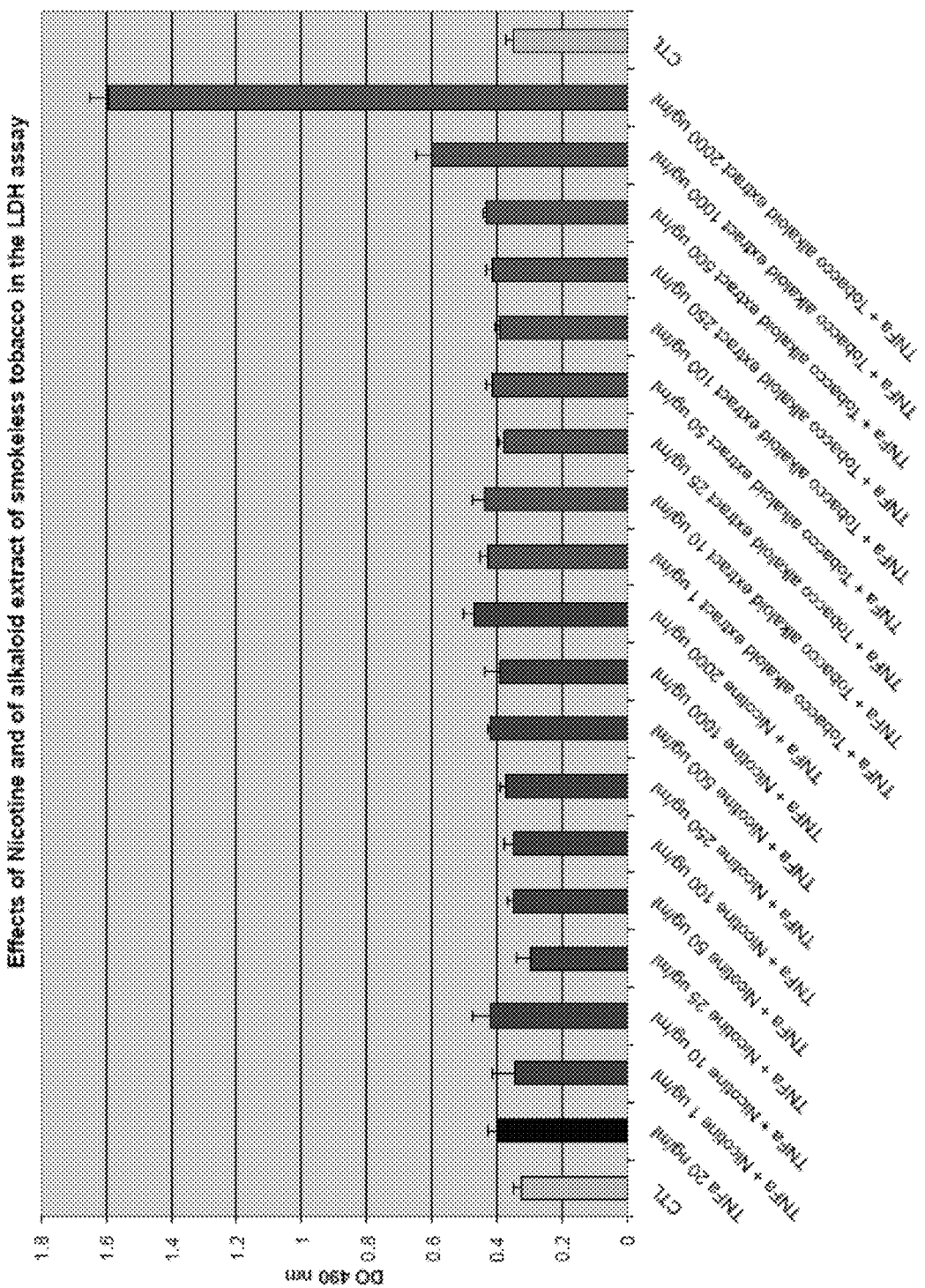
FIG. 6. Graph showing the results of a cytotoxicity assay using supernatant from the cells assayed in FIG. 3.

Although not suitable for administration as pharmaceuticals, both nicotine and an alkaloid extract of smokeless tobacco reduce TNFα-induced NFκB-mediated transcription (FIG. 3); at higher doses, the alkaloid extract demonstrates pronounced cytotoxicity (FIG. 6).

Example 2

Figure 7:
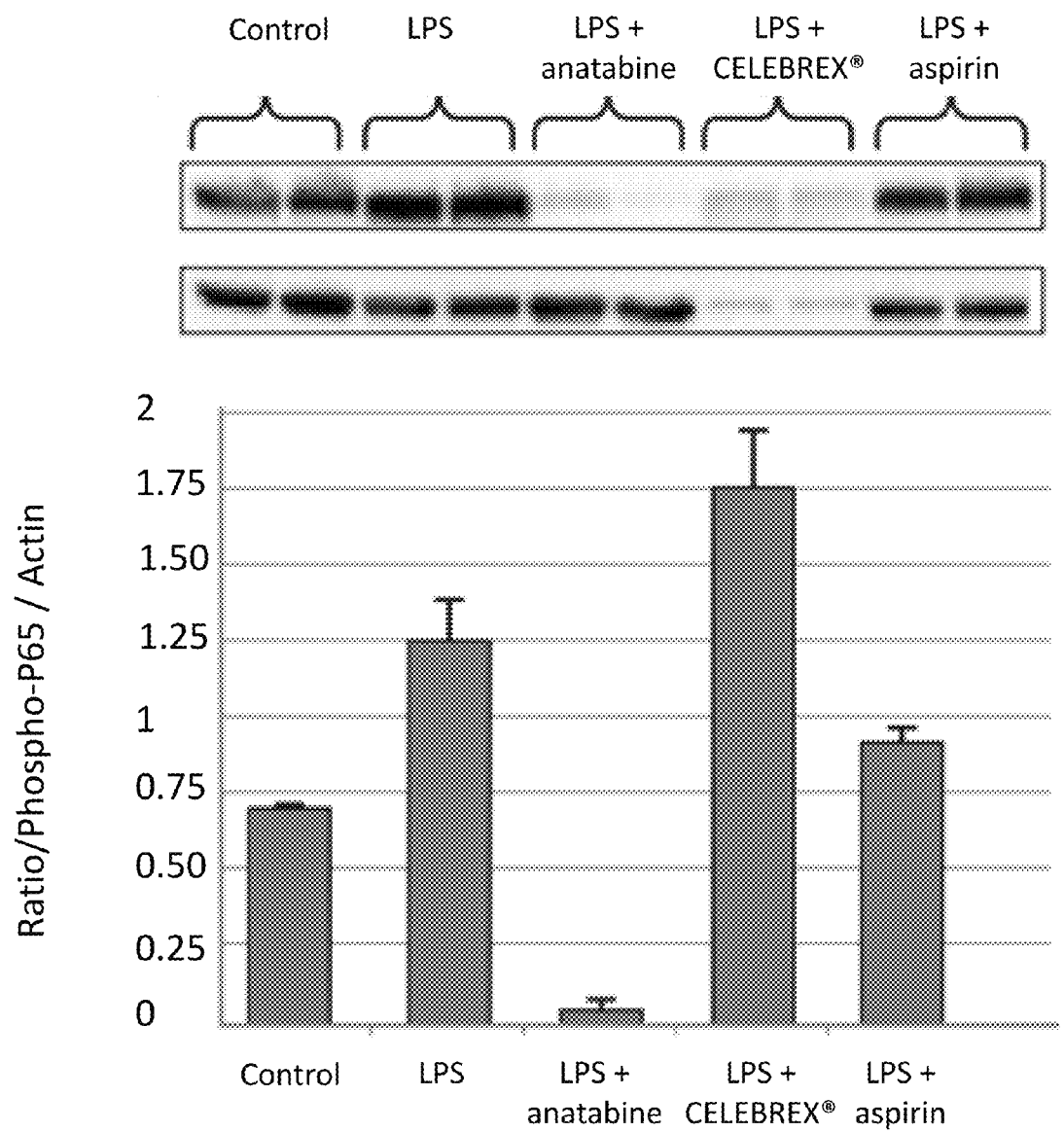
FIG. 7. Graph comparing effects of anatabine, CELEBREX®, and aspirin on lipopolysaccharide (LPS)-induced NFκB activity in human white blood cells.

Effects of Anatabine, CELEBREX®, and Aspirin on LPS-Induced NFκB Activity in Human White Blood Cells Peripheral blood mononuclear cells were isolated using the Ficoll plaque method according to the manufacturer's instructions. The cells were activated with LPS 10 μg/ml and treated with 1.25 mM anatabine, celecoxib (CELEBREX®), or aspirin. Cells were then incubated at 37° C. and 5% $CO_2$ overnight (18 hours) in RPMI medium supplemented with 20 mg/ml PHA, 1% penicillin/streptomycin, and 1% glutamax and assayed to detect NFκB activity. The results are shown in FIG. 7.

Example 3

Figure 8:
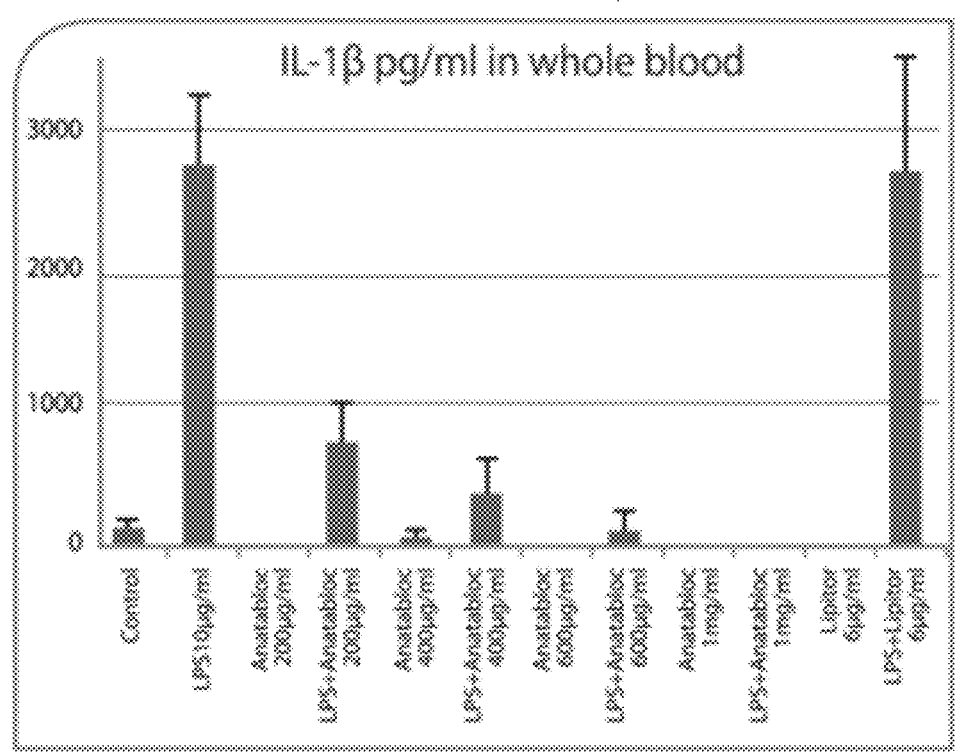
FIG. 8. Graph demonstrating effects of increasing concentrations of anatabine ("anatabloc" in the figure) on the release of interleukin 1-beta (IL-1β) from human blood cells.
Figure 9:
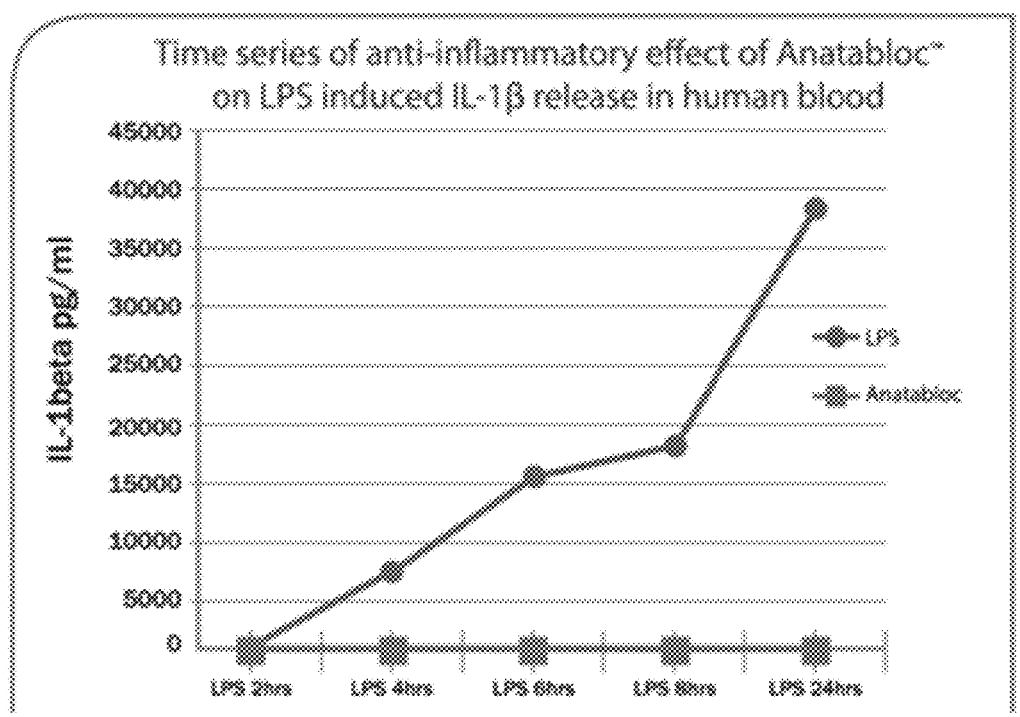
FIG. 9. Graph demonstrating time course of effect of anatabine ("anatabloc" in the figure) on the release of interleukin 1-beta (IL-1β) from human blood cells.

Effects of Increasing Concentrations of Anatabine on IL-1β Release from Human Blood Cells Stimulation of human blood cells with LPS causes release of interleukin 1β (IL-1β). Anatabine inhibits this release in a concentration-dependent manner, as shown in FIG. 8. FIG. 9 is a graph demonstrating this inhibition over time.

Example 4

Figure 10:
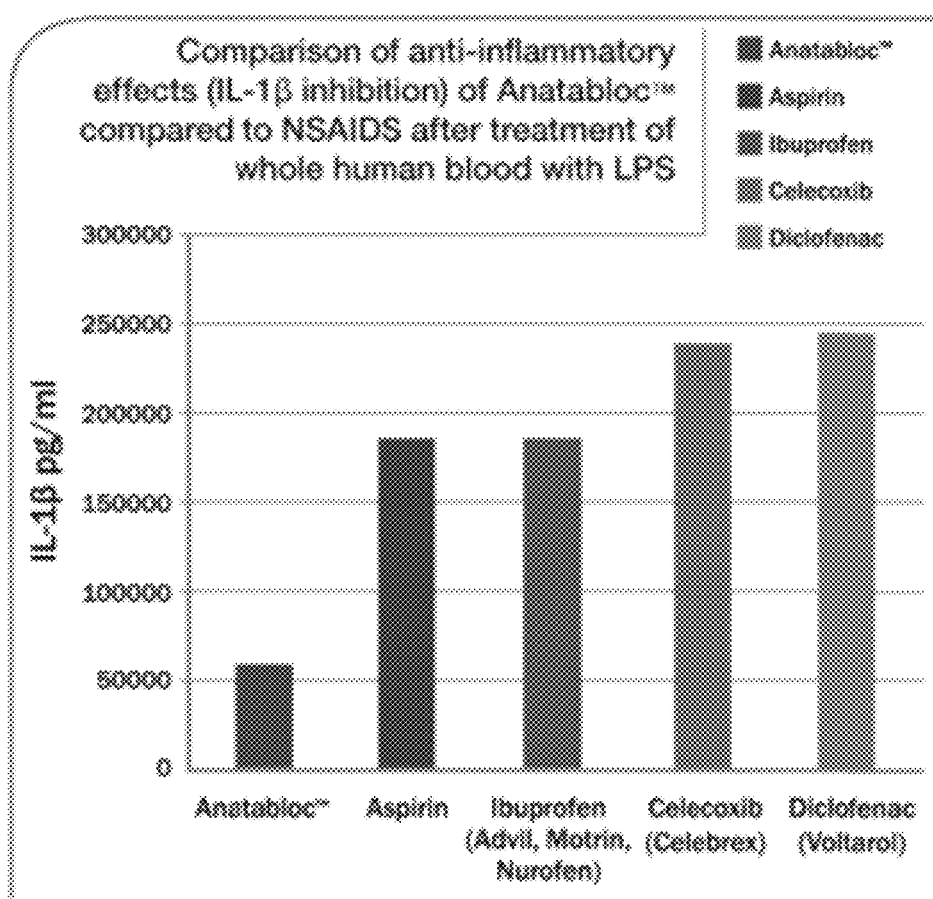
FIG. 10. Graph demonstrating effects of anatabine, aspirin, ibuprofen, celecoxib, and diclofenac on IL-1β accumulation after treatment of whole human blood with LPS.

Effects of Anatabine, Aspirin, Ibuprofen, Celecoxib, and Diclofenac on IL-1β Accumulation after Treatment of Whole Human Blood with LPS Whole human blood was treated with LPS (to stimulate IL-1β production) and either anatabine, aspirin, ibuprofen, celecoxib, or diclofenac. After 16 hours, IL-1β release was measured. The results are shown in FIG. 10 and demonstrate a reduced accumulation of IL-1β in anatabine-treated blood compared with blood treated with other anti-inflammatory agents.

Example 5

Dietary Supplement Formulation

A dietary supplement was prepared by combining the components listed in Table 2 below and forming into 160 mg tablets containing 1 mg anatabine, 417 IU Vitamin A (as retinyl acetate), and 33 IU Vitamin D3 (as cholecalciferol). Anatabine citrate was prepared synthetically as described in Examples 1-3 of co-pending application Ser. No. 12/729,346, which is incorporated herein by reference in its entirety. A granulation was made containing 1.003 mg free base anatabine (Davos/Anthem), 1.003 mg citric acid anhydrous (Spectrum Chemical Mfg. Corp.), 0.090 mg BHT (Spectrum Chemical Mfg. Corp.), and 17.958 mg mannitol (Roquette) and combined with the ingredients in Table 2.

TABLE 2

| Material | Amount (mg/tablet) | Amount (wt. %) |
|---|---|---|
| Anatabine granulation | 20 | 12.5 |
| Mannitol | 123.8 | 77.375 |
| Sucralose | 3.2 | 2.0 |
| Flavors | 7.2 | 4.5 |
| Vitamin A Acetate | 1.0 | 0.625 |
| Vitamin D3 | 0.4 | 0.250 |
| Fumed Silica | 1.6 | 1.0 |
| Stearic Acid | 2.0 | 1.25 |
| Magnesium stearate | 0.8 | 0.50 |
| Total | 160.0 | 100 |

The invention claimed is:

1. A method of providing anti-inflammation support, comprising administering to an individual in need thereof a lozenge comprising anatabine in an amount of about 1 mg, Vitamin A in an amount of about 417 IU, and Vitamin D3 in an amount of about 33 IU.

2. The method of claim 1, wherein the product further comprises one or more additional ingredients selected from the group consisting of mannitol, natural mint flavors, artificial mint flavors, sucralose, silicon dioxide, stearic acid, hydroxypropyl methylcellulose, magnesium stearate, titanium dioxide, natural glaze, methyl parabens, propylparabens, triethyl citrate, citric acid, BHT, mono and diglycerides, and polysorbate 80.

3. A product in the form of a lozenge comprises anatabine in an amount of about 1 mg, retinyl acetate in an amount of about 417 IU, and chalecalciferol in an amount of about 33 IU.

4. The method of claim 3, wherein the product further comprises one or more additional ingredients selected from the group consisting of mannitol, natural mint flavors, artificial mint flavors, sucralose, silicon dioxide, stearic acid, hydroxypropyl methylcellulose, magnesium stearate, titanium dioxide, natural glaze, methyl parabens, propylparabens, triethyl citrate, citric acid, BHT, mono and diglycerides, and polysorbate 80.

* * * * *